United States Patent [19]

Kanzaki et al.

[11] 4,261,978

[45] Apr. 14, 1981

[54] TREATMENT AND PROPHYLAXIS OF SWINE DYSENTERY

[75] Inventors: Toshihiko Kanzaki, Takarasuka; Toshiyuki Yamazaki, Kawanishi, both of Japan

[73] Assignee: Takeda Chemical Industries, Ltd., Osaka, Japan

[21] Appl. No.: 57,375

[22] Filed: Jul. 13, 1979

[30] Foreign Application Priority Data

Jul. 14, 1978 [JP] Japan .................................. 53/86586

[51] Int. Cl.$^3$ ............................................ A61K 31/34
[52] U.S. Cl. .................................... 424/122; 424/283
[58] Field of Search ........................ 424/122, 121, 283

[56] References Cited

U.S. PATENT DOCUMENTS

| | | | |
|---|---|---|---|
| 4,027,034 | 5/1977 | Messersmith | 424/283 |
| 4,069,316 | 1/1978 | Imada et al. | 424/121 |

OTHER PUBLICATIONS

Imada et al., The Journal of Antibiotics (Tokyo), vol. 31, No. 1, pp. 7 to 14 (1978).

Primary Examiner—John D. Randolph
Attorney, Agent, or Firm—Wenderoth, Lind & Ponack

[57] ABSTRACT

Carriomycin and physiologically acceptable salts thereof are effective for the treatment and prophylaxis of swine dysentery.

8 Claims, No Drawings

TREATMENT AND PROPHYLAXIS OF SWINE DYSENTERY

The present invention relates to treatment and prophylaxis of swine dysentery.

Swine dysentery is an epidemic intestinal disease in pigs, as caused by *Treponema hyodysenteriae* a dominant symptom of which is bloody mucous diarrhea. The high incidence of this disease has been observed in most of the countries where pigs are raised and once there is an outbreak, the disease becomes ubiquitous in the area and is extremely difficult to eradicate. Therefore, wherever large herds are kept, feed efficiencies are reduced so much as to cause serious economic losses.

Various drugs have heretofore been employed for the prophylaxis and treatment of swine dysentery but none has proved fully satisfactory because some of them are not sufficiently effective while others are accompanied by serious untoward effects or are suspicious of safety, especially of carcinogenesis.

The research undertaken against the above technical background led the present inventors to the unexpected finding that carriomycin displays a marked prophylactic and therapeutic action on swine dysentery, which has never been obtained with the drugs hitherto used. The finding was followed by a further research which has culminated in the development of this invention.

Thus, the principal object of this invention is to provide a method for the prophylaxis or treatment of swine dysentery, which comprises administering to pig carriomycin or a physiologically acceptable salt thereof, and another object is to provide a composition for the prophylaxis and treatment of swine dysentery containing carriomycin or the salt thereof. Other objects will be made clear from the description and claims presented hereinafter.

Carriomycin is a polyether antibiotic which is called also as Antibiotic T-42082 and the properties of the producers of this antibiotic, the method of producing it and its physicochemical and antibacterial as well as anticoccidial properties have been described in detail, for example in the specification of U.S. Pat. No. 4,069,316 and The Journal of Antibiotics (Tokyo) Vol.31, No.1, p.p.7-14(1978). As one of the carriomycin-producing microorganisms, *Streptomyces hygroscopicus* T-42082 has been deposited at the Institute for Fermentation, Osaka, Japan, and American Type Culture Collection, U.S.A., under the accession numbers of IFO-13609 and ATCC-31080, respectively.

According to the present invention, carriomycin may be employed as the free acid from or in the form of a physiologically acceptable salt, such as a salt with physiologically acceptable bases, e.g. alkali metal salts (sodium salt, potassium salt, etc.) and alkaline earth metal salts (calcium salt, etc.).

The anti-swine-dysentery agent according to this invention may be prepared by formulating carriomycin or a salt thereof into such dosage forms as powders, dusts, granules, tablets, liquid, capsules, etc. either together with a solid or liquid diluent or without a diluent, or by adding carriomycin or a salt thereof to feed or drinking water either directly or after having been dispersed into a diluent to prepare a premix. The diluent may be any of the known physiologically harmless diluents and is preferably one of those which may be routinely used as a feed or a feed component for pig. As the solid diluent or carrier, there may be mentioned barley flour, wheat flour, rye flour, corn meal, soybean meal, rape-seed cake, rice hull, rice bran, defatted rice bran, sweet potato meal, white potato meal, soybean curd cake, starch, lactose, sucrose, glucose, fructose, yeast, spent yeast, fish meal, talcum, acid white clay, clay and so on.

The liquid carrier may be example be water, physiological saline or one of physiologically harmless organic solvents. In addition, other suitable auxiliary agents such as emulsifier, dispersing agent, suspension aid, wetting agent, gelling agent, solubilizer, etc. may also be incorporated in proper proportions. It is also possible to incorporate a preservative, fungicide, antibiotic, enzyme preparation, Lactobacillus preparation, vitamins, minerals, amino acids, etc.

The proper dosage of the anti-swine dysentery agent of this invention depends on conditions, route of administration, etc. Generally, carriomycin or a salt thereof is orally administered to pig in an amount of about 0.5 to 13 mg. (All the quantitative indications of carriomycin or a salt thereof as given hereinafter are in terms of its free acid form) per kilogram body weight daily. More particularly, for the prophylaxis of swine dysentery carriomycin or a salt thereof is advantageously administered to pig susceptible to swine dysentery at the dose level of about 0.5 to 9 mg. per kilogram body weight daily. In this application, it is practical to orally administer ad libitum to pig a feed containing carriomycin or a salt thereof in a weight concentration of about 2 to 200 ppm. and, preferably, about 10 to 100 ppm. For the treatment of swine dysentery, the anti-swine dysentery agent of this invention is desirably administered at the dose level of about 0.8 to 13 mg. in terms of carriomycin per kilogram body weight daily. In this case, it is advantageous to orally administer ad libitum to pig infected with the dysentery a feed containing carriomycin or its salt in a weight concentration of about 10 to 500 ppm., especially 15 to 150 ppm.

Compared with other similar drugs, carriomycin used in the practice of this invention has the following desirable characteristics.

(A) Carriomycin displays very potent antibiotic activity against *Treponema hyodysenteriae*, the causative organism of swine dysentery, which is 10 to 100 as much effective as other polyether antibiotics. This data is a collaborative evidence of the prophylactic and therapeutic efficacy of this agent against swine dysentery. Table 1 shows the minimum inhibitory concentrations of carriomycin and other representative polyether antibiotics against the causative organisms of swine dysentery as assayed in accordance with the Method for Assaying the Susceptibility of *Treponema hyodysenteriae* to Drugs as proposed by Kashiwazaki et al [Proceedings of the 82nd General Meeting of Japan Veterinary Society, p. 101 (1976)].

TABLE 1

| Drug | Minimum inhibitory concentration (MIC: µg./ml.) | | | |
|---|---|---|---|---|
| Strain | MK 1 | MK 2 | MK 4 | OX 1 |
| Carriomycin | 0.1 | 0.1 | 0.1 | 0.1 |
| Lasalocid A | 10 | 10 | 10 | 10 |
| Salinomycin | 1 | 1 | 0.1 | 1 |

TABLE 1-continued

| Drug | Strain Minimum inhibitory concentration (MIC: μg./ml.) | | | |
|---|---|---|---|---|
| | MK 1 | MK 2 | MK 4 | OX 1 |
| Monensin | 1 | 1 | 1 | 1 |

(1)Strains: These strains belong to Treponema hyodysenteriae isolated from the bloody mucous faeces of dysenteric pigs; MK 1, MK 2 and MK 4 were obtained in Kyushu District of Japan while OX 1 was obtained in Okinawa, Japan.
(2)Antimicrobial potency assay: Agar Dilution Method
(3) Inoculum size: a loopful of $10^6$ CFU/ml.
(4)Cultural conditions: Gas Pak (BBL) method, 37° C., 2 days (B) Carriomycin is highly safe because it is sparingly absorbed from the digestive tract, thus leaving substantially no residue in the animal body.

(C) Carriomycin is extremely low in toxicity to animals. The $LD_{50}$ value of Carriomycin (mouse, oral) is about 2,000 mg./kg. which means that it is considerably less toxic than other polyether antibiotics such as salinomycin ($LD_{50}$=50 mg./kg., mouse, oral) and Lasalocid A ($LD_{50}$=146 mg./kg., mouse, oral.) This fact not only indicates high safety to human beings in production and distribution but also means a greater tolerance of the animals medicated. Thus, when carriomycin is administered as incorporated in feed, even a fair degree of unhomogeniety in the admixing stage does not detract appreciably from the safety of the agent to subject animals.

By administering carriomycin or a salt thereof according to this invention, an excellent prophylaxis and treatment of swine dysentery can be accomplished and consequently the growth of the pigs can be significantly promoted.

The following Examples are given merely to illustrate this invention in detail and should by no means be construed to limit the scope of the invention.

Throughout the present specification as well as in claims, the abbreviations "μg.", "mg.", "g.", "kg.", "ml.", "IU" and "ppm." respectively refer to "microgram(s)", "milligram(s)", "gram(s)", "kilogram(s)", "international unit(s)" and "part(s) per million", and percentages are by weight unless otherwise specified.

EXAMPLE 1

A premix containing 10% of carriomycin monosodium salt crystals as diluted with finely milled soybean meal was added to a feedstuff and pigs were allowed to take the feed as libitum. The feed was the proprietary pig starter mentioned in Example 2 without added antibiotics. The pigs were SPF LW and used in groups of 4 animals (2 male and 2 female.)

The pigs were infected as follows. Thus, Treponema hyodysenteriae was anaerobically grown on a 5% horse blood agar plate and the resultant culture was homogenized and admixed with 3% mucin-phosphate buffer. The mixture was directly administered into the stomach of each SPF pig. From each of the pigs showing typical symptoms of swine dysentery, the colon content and mucous membrane were taken and diluted two-fold with 3% mucin-phosphate buffer to obtain a final infective material. An 80 ml. portion of this preparation was directly infused into the stomach of each test pig, which was then put on the unmedicated feed for the initial six days. Beginning with the 7th day, each pig was put on the feed medicated with one of predetermined concentrations of the test drug and was reared for a total of 28 days. Tests were performed for three groups of animals dosed with 0 ppm. 15 ppm. and 150 ppm., respectively, of carriomycin. The results are summarized in Table 2.

TABLE 2

| | | Group | | |
|---|---|---|---|---|
| | | A | B | C |
| Dose of carriomycin (con. in feed) | (ppm.) | 0 | 15 | 150 |
| Number of pigs | (heads) | 4 | 4 | 4 |
| Mean body weight at infection | (kg./head) | 15.2 | 14.5 | 15.5 |
| Mean body weight at end of test | (kg./head) | 18.0 | 29.1 | 31.7 |
| Mean weight gain | (kg./head) | 2.8 | 14.6 | 16.2 |
| Mean feed intake | (kg./head) | 19.9 | 36.5 | 37.3 |
| Mean feed conversion ratio | | 7.1 | 2.5 | 2.3 |
| Mean number of days with diarrhea | (days/head) | 20.8 | 3.0 | 1.5 |
| Mean number of days with bloody mucous faeces | (days/head) | 15.0 | 0.5 | 0.1 |

It will be apparent from Table 2 that carriomycin brings about considerable increases in body weight gain and considerable improvements in feed conversion ratio, the number of days with diarrhea and the number of days with bloody mucous faeces, thus showing very desirable effects on swine dysentery.

EXAMPLE 2

By incorporating carriomycin or a salt thereof in the following basal feed at optional concentration, antiswine-dysentery agents or premixes according to this invention can be produced.

TABLE 3

| | Composition of basal feed (%) | |
|---|---|---|
| Materials | Pig starter | New feed for progeny test of meat production |
| Corn | 20.0 | 22.0 |
| Milo | | 22.0 |
| Barley flour | 19.0 | 22.0 |
| Wheat flour | 14.0 | |
| Toasted soybean flour | 4.0 | |
| Wheat bran | 6.8 | 12.0 |
| Defatted rice bran | 4.0 | 4.0 |
| Fish meal | 3.0 | 4.0 |
| Dried skim milk powder | 9.78 | |
| Soybean meal | 5.0 | 4.0 |
| Dried whey | 5.0 | |
| Alfalfa meal | | 2.5 |
| Dextrose | 5.0 | |
| Yeast for feed | 2.0 | |
| Powdered fat | 1.5 | |
| Calcium carbonate | | 1.5 |
| Sodium chloride | | 0.5 |
| Calcium tertiary phosphate | 0.7 | 0.8 |
| Saccharine | 0.02 | |
| Vitamin-mineral mixture | 0.2[a] | 0.4[b] |
| DL-methionine | | 0.1 |

[a]Contains per kilogram: 2,500,000 IU of vitamin A, 500,000 IU of vitamin $D_3$, 0.75 g. of vitamin E, 1 g. of vitamin $B_1$ . nitrate, 1.5 g. of vitamin $B_2$, 0.25 g. of vitamin $B_6$, 1 mg. of vitamin $B_{12}$, 3.5 g. of calcium pantothenate, 7.5 g. of nicotinamide, 50 g. of choline chloride, 50 g. of iron, 5 g. of copper, 25 g. of zinc, 15 g. of manganese, 0.25 g. of cobalt and 0.1 g. of iodine.
[b]The following mixtures A, B and C are admixed in a ratio of 0.15: 0.15: 0.1 by weight.
Mixture A: 5% of manganese, 5% of iron, 1% of copper, 6% of zinc and 0.1% of iodine
Mixture B: 10,000 IU of vitamin A and 2000 IU of vitamin $D_3$ per gram
Mixture C: 1g. of vitamin $B_1$ . nitrate, 7 g. of vitamin $B_2$, 0.5 g of vitamin $B_6$ 6 g. nicotinamide, 10.9 g. of calcium pantothenate and 57.6 g. of choline hydrochloride per kilogram; supplemented with 10 μg. of vitamin $B_{12}$.

What is claimed is:

1. A method for the prophylaxis or treatment of swine dysentery, which comprises administering to pig an effective amount of carriomycin or a physiologically acceptable salt thereof.

2. A method according to claim 1, wherein carriomycin or a physiologically acceptable salt is orally administered at the dose level of about 0.5 to 13 mg. in terms of free carriomycin per kilogram body weight daily.

3. A method according to claim 1, wherein a feed containing carriomycin or a physiologically acceptable salt thereof is orally administered ad libitum for the prophylaxis to pig susceptible to swine dysentery.

4. A method according to claim 3, wherein the feed contains carriomycin or a physiologically acceptable salt thereof in a weight concentration of about 2 to 200 ppm. in terms of free carriomycin.

5. A method according to claim 1, wherein a feed containing carriomycin or a physiologically acceptable salt thereof is orally administered ad libitum for the treatment to pig infected with swine dysentery.

6. A method according to claim 5, wherein the feed contains carriomycin or a physiologically acceptable salt thereof in a weight concentration of about 10 to 500 ppm. in terms of free carriomycin.

7. A method according to claim 1, wherein the physiologically acceptable salt is an alkali metal salt or an alkaline earth metal salt.

8. A method according to claim 1, wherein free carriomycin is administered.

* * * * *